(12) United States Patent
Lim et al.

(10) Patent No.: US 10,736,743 B2
(45) Date of Patent: Aug. 11, 2020

(54) HANDLE ASSEMBLY FOR IMPLANT DELIVERY APPARATUS COMPRISING A FORCE LIMITER, A DISPLACEMENT LIMITER AND/OR A BRAKE FRAME ASSEMBLY

(71) Applicant: VENUS MEDTECH (HANGZHOU), INC., Hangzhou (CN)

(72) Inventors: Hou-Sen Lim, Singapore (SG); Wolfgang Gotz, Regensburg (DE)

(73) Assignee: Venus Medtech (Hangzhou) Inc., Hangzhou (CN)

( * ) Notice: Subject to any disclaimer, the term of this patent is extended or adjusted under 35 U.S.C. 154(b) by 663 days.

(21) Appl. No.: 14/909,063

(22) PCT Filed: Jul. 31, 2014

(86) PCT No.: PCT/EP2014/066478
§ 371 (c)(1),
(2) Date: Jan. 29, 2016

(87) PCT Pub. No.: WO2015/014931
PCT Pub. Date: Feb. 5, 2015

(65) Prior Publication Data
US 2016/0184097 A1    Jun. 30, 2016

(30) Foreign Application Priority Data
Jul. 31, 2013  (EP) ..................................... 13178717

(51) Int. Cl.
*A61F 2/06*   (2013.01)
*A61F 2/24*   (2006.01)
*A61F 2/95*   (2013.01)

(52) U.S. Cl.
CPC .............. *A61F 2/2439* (2013.01); *A61F 2/95* (2013.01); *A61F 2002/9511* (2013.01); *A61F 2002/9517* (2013.01)

(58) Field of Classification Search
CPC ................ A61F 2002/9515; A61F 2/95; A61F 2002/9534; A61F 2/962; A61F 2/966;
(Continued)

(56) References Cited

U.S. PATENT DOCUMENTS 3,777,591 A * 12/1973 Thomasian ............. F16H 27/06
                                                           192/139
5,600,874 A *  2/1997 Jungkind ............... A43C 11/16
                                                           24/68 SK
(Continued)

FOREIGN PATENT DOCUMENTS

EP    2382947 A1   11/2011

OTHER PUBLICATIONS

PCT/EP2014/066478, International Search Report, dated Nov. 5, 2014.

*Primary Examiner* — Darwin P Erezo
*Assistant Examiner* — Erin L Colello
(74) *Attorney, Agent, or Firm* — Raymond Sun

(57) ABSTRACT

The present invention relates to a handle assembly (100) for an implant delivery device for folding or unfolding at least one medical implant by means of at least one tension thread, wherein the handle assembly (100) comprises a drum (14) for winding the tension thread thereon by rotating the drum (14); a knob (9) to be rotated by a user of the handle assembly (100) in order to fold or unfold the medical implant, the knob (9) being interconnected with the drum (14) such that the drum (14) is rotated when the knob (9) is rotated; and a displacement limiter for limiting the length or displacement by which the tension thread (11) may be at
(Continued)

least one of wound onto or unwound from the drum (14) by rotating the knob (9).

19 Claims, 22 Drawing Sheets

(58) Field of Classification Search
CPC ............ A61F 2002/9665; A61F 2/2427; A61F 2/2436; A61F 2/2439; A61F 2002/9517; A43C 11/165; A61M 25/0136; A61M 25/0147; F16H 27/06; F16H 19/0672
See application file for complete search history.

(56) References Cited

U.S. PATENT DOCUMENTS

| | | | | |
|---|---|---|---|---|
| 6,033,412 | A * | 3/2000 | Losken | A61B 17/663 606/105 |
| 7,824,443 | B2 * | 11/2010 | Salahieh | A61F 2/2439 623/2.11 |
| 8,366,760 | B2 * | 2/2013 | Kumoyama | A61F 2/95 623/1.11 |
| 8,500,789 | B2 * | 8/2013 | Wuebbeling | A61F 2/95 606/108 |
| 2005/0081339 | A1 * | 4/2005 | Sakabayashi | A43C 7/00 24/128 |
| 2005/0085851 | A1 * | 4/2005 | Fiehler | A61B 17/0057 606/213 |
| 2006/0173524 | A1 * | 8/2006 | Salahieh | A61F 2/2439 623/1.11 |
| 2006/0259124 | A1 * | 11/2006 | Matsuoka | A61F 2/966 623/1.12 |
| 2006/0282150 | A1 * | 12/2006 | Olson | A61F 2/966 623/1.11 |
| 2007/0088421 | A1 * | 4/2007 | Loewen | A61F 2/95 623/1.11 |
| 2007/0168014 | A1 * | 7/2007 | Jimenez | A61F 2/95 623/1.12 |
| 2008/0071311 | A1 * | 3/2008 | White | A61B 17/0057 606/232 |
| 2010/0076541 | A1 * | 3/2010 | Kumoyama | A61F 2/95 623/1.11 |
| 2010/0174290 | A1 * | 7/2010 | Wuebbeling | A61F 2/95 606/108 |
| 2010/0234883 | A1 * | 9/2010 | White | A61B 17/0057 606/213 |
| 2011/0172702 | A1 * | 7/2011 | Fiehler | A61B 17/0057 606/213 |
| 2012/0022635 | A1 * | 1/2012 | Yamashita | A61F 2/95 623/1.12 |
| 2012/0330401 | A1 * | 12/2012 | Sugimoto | A61F 2/915 623/1.12 |

\* cited by examiner ics/# HANDLE ASSEMBLY FOR IMPLANT DELIVERY APPARATUS COMPRISING A FORCE LIMITER, A DISPLACEMENT LIMITER AND/OR A BRAKE FRAME ASSEMBLY The present invention relates to a handle assembly and to an implant delivery apparatus.

From WO 2009/109348 A1, implants are known that can be folded and/or unfolded by means of one or more threads transferring tension onto the implant. Furthermore, respective apparatuses for folding and unfolding are known from above mentioned patent application. Such apparatuses are used for both delivering the implant and folding and unfolding the implant. Folding and unfolding usually takes place by means of a handle assembly comprising a tensioning device for amending the force with which tension threads act on the implant.

One object of the present invention is to propose a further handle assembly for an delivery apparatus used for delivering an implant that may be folded or unfolded by means of a tension thread. Furthermore, an appropriate implant delivery apparatus is proposed.

This object may be solved in the most general way by a handle assembly comprising at least one of a force limiter, a displacement limiter and a brake frame assembly.

Further, this object may be solved by any arbitrary combinations of features disclosed below. In particular, this object may be solved by means of a handle assembly according to the present invention. It also may be solved by an apparatus according to the present invention.

Advantageous embodiments or developments of the apparatus according to the present invention are each subject matter of the dependent claims.

Embodiments according to the present invention may each comprise one or more of the features disclosed above and/or in the following in any arbitrary combination.

Thus, according certain embodiments according to the present invention, a handle assembly for an implant delivery device for folding or unfolding at least one medical implant by means of at least one tension thread is suggested. The handle assembly comprises a drum for winding the tension thread thereon by rotating the drum. It further comprises a knob to be rotated—or being arranged to be rotatable relative to another section of the handle assembly—by a user of the handle assembly in order to fold or unfold the medical implant by tightening or winding the tension thread or by releasing or unwinding the tension thread. The knob is arranged with or interconnected with the drum such that the drum is rotated when the knob is rotated.

The handle assembly further comprises a displacement limiter for limiting the length or displacement by which the tension thread may be at least one of wound onto or unwound from the drum by rotating the knob.

Thus, according to particular embodiments of the present invention, a handle assembly for an implant delivery device for folding or unfolding at least one medical implant by means of at least one tension thread is proposed. The handle assembly comprises a drum for winding the tension thread thereon by rotating the drum. It further comprises a knob to be rotated by a user of the handle assembly in order to fold or unfold the medical implant. The knob is directly or indirectly interconnected with the drum such that the drum is rotated when (and/or because) the knob is rotated.

The handle assembly further comprises a force limiter for limiting the maximum force or tension that may be applied or is applicable to the tension thread or to the drum by rotating the knob.

Thus, according to particular embodiments of the present invention, a handle assembly for an implant delivery device for folding or unfolding at least one medical implant by means of at least one tension thread is proposed. The handle assembly comprises a drum for winding the tension thread thereon by rotating the drum. It further comprises a knob to be rotated by a user of the handle assembly in order to fold or unfold the medical implant by tightening or winding the tension thread or by releasing or unwinding the tension thread, the knob being arranged or interconnected with the drum such that the drum may be rotated when the knob is rotated. The handle assembly of this embodiment further comprises a brake frame assembly comprising at least one brake element and at least one spring arranged to act on the brake element such that the brake elements contact one surface of the rear knob.

The implant delivery apparatus according to the present invention comprises at least one handle assembly according to the present invention.

Whenever numerical values are mentioned herein such as "one", "two" and the like, they have to be understood as values representing the lower threshold of numerical ranges. A long as this does not result in a contradiction in the eyes of the skilled one, numerical values, such as "one" shall be understood as comprising also "at least one". This interpretation or understanding is as well encompassed by the present invention as the understanding according to which a numerical value such as "one" may be understood as "exactly one" whenever this appears technically possible to the skilled person. Both understandings are covered by the present invention. This applies to any numerical value stated herein.

In the following 'can/may be' or 'can/may have' and so forth has to be understood as 'preferably is' or 'preferably has' and so forth and is to be understood as be related to an embodiment according to the present invention.

In some embodiments according to the present invention, the handle assembly's knob comprises a gear pattern or teeth, e. g. on an inner rim of the knob. In these embodiments, the force limiter comprises or consists of a first ring element, e. g. a rush gear, comprising a gear pattern or teeth matching or corresponding to the gear pattern or teeth of the knob. Further, the force limiter comprises at least one spring element arranged for pressing the first ring element against the knob in a manner such that when a user rotates the knob, in an assembled state of the handle assembly the first ring element is also rotated because of the interaction between the gear pattern or teeth of the knob on the one side and the gear pattern or teeth of the first ring element on the other side.

In some embodiments according to the present invention, the handle assembly's first ring element comprises teeth on an inner surface thereof.

In some embodiments according to the present invention, the force limiter further comprises a second ring element, e. g. a clutch stopper or a drive wheel. In these embodiments, the spring element is interposed between the first ring element and the second ring element and has contact to both of them.

In some embodiments according to the present invention, one of the first and the second ring element comprises protrusions, and the other one comprises or receptions arranged for receiving the protrusions so as to establish at least one of a form fit and a force disclosure between the first and the second ring elements.

In some embodiments according to the present invention, some or all of the receptions and the protrusions, respectively, are each arranged at on lower surface of the first ring element and on the upper surface of the second ring element.

In some embodiments according to the present invention, the force limiter further comprises an internal retaining ring attached within the inner lumen of the knob.

In some embodiments of the present invention, altering a form or shape of the implant means reducing or increasing a diameter, in particular an outer diameter, of the implant. Alterations of the diameter may be accompanied by any kind of alteration of the implant's length or any other alteration, or may be not.

In some embodiments according to the present invention, the drum and the knob are interconnected by a rush gear. The rush gear is arranged to rotated inside—and preferably in engagement with—a gear stopper. The gear stopper, which is preferably arrange inside the rear knob but preferably not fixed or interconnected to the rear knob resulting in that the gear stopper and the rear knob can rotate independently from each other, is moved along or by means of a gear pattern or teeth when being rotated. The rush gear is interconnected to the drum or to part of it such that a rotation of the rush gear results in a rotation of the drum. The displacement limiter comprises or consists of a ring-shaped or tube-shaped element—e.g. a gear stopper—having an inner surface. The inner surface comprises at least one of a second section having an inner surface different to the inner surface of the first section or a radial width (being the distance between the outer surface of the section and the inner surface thereof) smaller than that of the first section, and a third section having an inner surface different to the inner surface of the first section or a radial width smaller than that of the first section.

In some embodiments according to the present invention, at least one of the second section and the third section does not comprising teeth or a gear pattern.

In some embodiments according to the present invention, at least one of the second section and the third section is arranged in contact with the first section. Alternatively, at least one of them is arranged adjacent to the first section.

In some embodiments according to the present invention, the ring-shaped or tube-shaped element also comprises at least a fourth section on its inner surface. Preferably, the fourth section does not comprise teeth. The fourth section preferably does not comprise teeth or a gear pattern. The fourth section is separated or delimited from at least one of the first or second section by an inclination, an edge, a stop or a protrusion configured to prevent the rush gear to be rotated further towards to or onto the fourth section.

In some embodiments according to the present invention, the inner surface of at least one of the second section and the third section has a radial distance to the center of the ring-shaped or tube-shaped element that is larger than a radial distance between the tips of one, some, or the majority of the teeth and the center of the ring-shaped element.

In some embodiments according to the present invention, the ring-shaped or tube-shaped element comprises at least a first protrusion arranged to interfere with a second protrusion of the casing assembly or any other element of the handle assembly so as to limit the rotation of the rush gear within the ring-shaped or tube-shaped element.

In some embodiments according to the present invention, the at least one first protrusion is arranged so as to protrude into an inner lumen of the ring-shaped or tube-shaped element.

In some embodiments according to the present invention, the at least one first protrusion is arranged between the second and the third sections or at the fourth section or opposite the first section of the ring-shaped or tube-shaped element or has its base at one of the aforementioned sites.

In some embodiments according to the present invention, the second section has at least one of a length, width (in a radial direction) and inclination such that the rush gear may be positioned inside the second section such that at least one tooth of the rush gear is engaged with at least one tooth of the teeth of the first section while at least one tooth of the rush gear is at the same time in contact with the inclination, the edge, stop or protrusion delimiting the second section from the fourth section or arranged within the second section.

In some embodiments according to the present invention, the third section has at least one of a length, width (in a radial direction) and inclination such that the rush gear may be positioned inside it such that one tooth of the rush gear is only half-engaged with at least one tooth of the teeth of the first section while other teeth of the rush gear are at the same time in contact with the inclination, the edge, stop or protrusion delimiting the third section from the fourth section or arranged within the second section. "Half-engaged" within the meaning of the present embodiments may be such that rotating the drum in one direction may not result into rotating the gear stopper as well, whereas rotating the drum in the opposite direction would necessarily result in an functional engagement of the teeth of the drum with the teeth of the first section of the gear stopper again. "Half-engaged" may be understood such that one tooth of the drum and the last tooth of the first section 1911 contact each other temporarily but slip over each over if the rush gear 16 is rotated in a first direction whereas the rush gear 16 and the gear stopper 19 get into normal teeth engagement if the rush gear 16 is rotated in the counter-direction.

In some embodiments according to the present invention, the drum is simultaneously engaged (or at least half-engaged as defined above) both to the rush gear and the gear stopper, or is in contact with both, preferably always.

In some embodiments according to the present invention, the brake frame assembly (25) is configured and arranged to brake a rotation of the rear knob (9) or to prevent the unintended rotation thereof.

In some embodiments according to the present invention, the at least one brake element is arranged on a frame of the brake frame assembly such that the brake element may pivot with respect to the frame.

In some embodiments according to the present invention, the brake frame assembly is arranged inside the rear knob.

In some embodiments according to the present invention, the brake frame assembly has two brake elements arranged opposite to each other.

In some embodiments according to the present invention, the implant delivery device is designed or embodied as a catheter, in particular a heart catheter, or comprising such a catheter.

In some embodiments according to the present invention, the implant delivery device comprises at least one implant connected with tension threads for the purpose of folding and/or unfolding or provided or prepared for being connected with tension threads.

In some embodiments according to the present invention, the implant is a stent or a heart valve arrangement.

In certain embodiments of the present invention, folding the implant means reducing the implant's diameter.

In some embodiments according to the present invention, unfolding is to be understood as increasing a diameter of the implant or as allowing the implant to increase in diameter by, for example a shape memory capability plus a sufficient release of the tension thread that would otherwise hinder the implant from returning into its original shape.

To "unfold" may, hence, in some embodiments according to the present invention be understood as actively releasing the tension acting on tension threads biasing the implant.

In certain embodiments according to the present invention, the implant's diameter is present in a plane perpendicular to a main flow direction of the implant, in case the implant is flown through by a fluid after its implantation.

In some embodiments of the present invention, the at least one tension thread is a thread or filament or yarn, respectively. It can be designed or embodied similar to a surgical sutural thread or it can be such a surgical sutural thread. It can be designed or embodied as a rope or a cord or twine or string, respectively. It can be designed or embodied as a chain comprising a plurality of chain members engaged with adjacent chain members.

In the following, whenever reference is made to a thread or tension thread, the terms may include a plurality of threads or tension threads as well insofar as a person skilled in the art recognizes the exchangeability of the terms.

In certain embodiments, the shaft of the apparatus is in at least one section thereof embodied rigidly. In some embodiments, the shaft of the apparatus is in at least one section thereof embodied such as to be bendable in one or more directions (i. e. it may be bent in a longitudinal direction or in a direction of the shaft's width, in both directions or in any other direction). In some embodiments, the shaft is extendable or stretchable. In other embodiments, the shaft is stiff or inflexible.

In some embodiments of the apparatus according to the present invention, during its implanted implantation state, the implant is able to be penetrated by fluids or is permeable for fluids, respectively, in its longitudinal direction. The terms "permeable" or "able to be penetrated" hereby refer to the ability of the implant to be penetrated or flown through by fluids.

In some embodiments of the apparatus according to the present invention, in the moment of unfolding or folding, the implant is loosely arranged or attached to or at or on a receiving area of the apparatus. In some embodiments according to the present invention, the implant is thereby connected with the receiving area only by means of the tension threads.

In certain embodiments of the apparatus according to the present invention, the tension thread comprises or consists of a bundle or a plurality of threads or thread elements.

In some embodiments according to the present invention, a shaft of the apparatus is permeable or patent (like a blood vessel) within its interior in at least sections of its longitudinal direction or along its entire length. In those embodiments, the shaft comprises a wall.

In certain embodiments, at least one of the tension threads (or all of them) is partly arranged within an inner space of the shaft and extends from there to an outside of the shaft through the shaft opening.

In some embodiments, at least one of the tension threads (or all of them) exits from an inner space of the shaft through one shaft opening. In other embodiments, at least one of the tension threads (or all of them) exits from the inner space through two or more shaft openings.

In certain embodiments according to the present invention, the at least one shaft opening is provided at or on the front surface of the shaft. In other embodiments according to the present invention, it is arranged at or on a circumferential surface or lateral surface area of the shaft. Preferably, the shaft opening is arranged in or within a tip area of the shaft or in or within a proximal area of the shaft.

In certain embodiments according to the present invention, the shaft comprises a plurality of shaft openings uniformly or non-uniformly distributed or arranged along or about a periphery or along or about a circumferential surface or lateral surface area of the shaft. Additionally or alternatively, the shaft openings may be dispersed along or about a longitudinal direction of the shaft. For example, in some embodiments according to the present invention, the shaft may have two or more shaft openings which are arranged under different distances between the respective opening and the tip or one end of the shaft.

In certain embodiments according to the present invention, the shaft is arranged such that they does no move relatively to the remaining apparatus according to the present invention in a longitudinal direction of the apparatus upon folding or unfolding the medical implant.

In some embodiments according to the present invention, tension threads for folding and/or unfolding the implant enter and/or exit through the shaft opening.

In some embodiments according to the present invention, the shaft may comprise individual shaft fibers as it is disclosed in WO 2012/084178, the respective disclosure is expressly incorporated herein by reference thereto. In particular embodiments according to the present invention, some or all features mentioned herein with respect to the shaft may also be comprised by some or all of the individual shaft fibers.

In some embodiments according to the present invention, neither the shaft nor sections thereof are arranged within the interior or material of a wall of an envelope, an outer boundary or limitation, or the like of the apparatus.

In some embodiments according to the present invention of the apparatus, the shaft comprises one or more shaft openings. The one or more tension threads can enter into and/or exit from the shaft through the shaft openings.

In certain embodiments according to the present invention, such shaft openings are solely provided or used for allowing tension threads to enter in or into and/or leave or exit from the shaft.

In some embodiments according to the present invention, the shaft is designed or embodied to comprise one or more through-openings (extending into a longitudinal direction of the shaft) or one or more hollow interiors. These through-openings or hollow interiors may allow guiding one or more tension threads through the shaft, e. g. from the tensioning device of the apparatus to a shaft opening or to an exit opening at the tip portion of the shaft.

In some embodiments according to the present invention, the tension threads are arranged within an interior of the shaft such that they can be shifted or moved relative to the shaft.

In some embodiments according to the present invention, the shaft and/or the tension threads do not comprise any devices for establishing a hook engagement with the implant.

In some embodiments according to the present invention, some or all of the tension threads are connected with the implant by solely entangling or entwining the implant or a part or section or portion thereof.

In some embodiments according to the invention, some or all of the tension threads, i.e. at least one tension thread, do not encompass the whole circumference of the implant. In certain embodiments according to the invention, one or more of the tension threads re-enter the lumen of the implant through apertures provided within the circumference or rim of the implant that are, for example, adjacent to the aperture through which the respective tension thread has exited from the lumen. In some embodiments according to the invention, some or all of the tension threads are provided to re-enter the lumen by an aperture provided in the rim that is different from the aperture through which the particular tension thread has exited from the lumen to an outside of the implant. In particular, any tension thread may re-enter the lumen by the next aperture, the next but one, next but two, next plus three, or the like, on the circumference or on the rim.

In some embodiments according to the present invention, the apparatus is designed or intended for folding and/or unfolding an implant designed as a stent or a heart valve arrangement.

In some embodiments of the set according to the present invention, the implant is a stent or a heart valve arrangement.

In certain exemplary embodiments according to the present invention, at least one of the apparatus and the implant comprises exclusively, i.e. only, (one or more) materials that are MRI (short for: magnetic resonance imaging) compatible. In certain exemplary embodiments according to the present invention, at least one of the apparatus and the implant comprises exclusively (one or more) materials that are not magnetic, ferromagnetic, or both. In some exemplary embodiments according to the present invention, at least one of the apparatus and the implant does not comprise metal or any metal alloy.

In some embodiments of the set according to the present invention, the implant is connected or intended to be interconnected with the apparatus by means of tension threads such that the tension threads may act and/or contact the medical implant not only at one end of the medical implant but at least at two or more sections of the medical implant which are longitudinally offset from each other.

In some embodiments according to the present invention, the handle assembly does not comprise an indicator for indicating the position of an actuation element, for example of a tension thread, in particular no indicator to be aligned with some markings of the handle assembly.

In certain embodiments according to the present invention, the displacement limiter is not designed and/or does not comprise a Geneva-gear mechanism or a Maltese-cross, in particular not of the circumscribed type.

In some embodiments according to the present invention, the displacement limiter does not comprise a band, in particular of a predetermined length, intended and/or configured to be wound around an axis or spool configured to rotate when the drum is rotated and/or during the winding/unwinding of the tension thread.

The advantages achievable by means of some or all embodiments of the handle assembly according to the present invention may also be achieved by means of the apparatus according to the present invention.

Some or all of the following advantages and the advantages mentioned above can be achieved in some, certain or all embodiments according to the present invention.

In some embodiments according to the present invention, one achievable advantage is that the force applied on the tension threads by which the implant is folded or unfolded may not be exceeded. Hence, the risk of a tension thread rupture because of undue operation of the handle assembly is minimized or even completely avoided because of the force limiter. In fact, the tension the tension threads have to stand upon winding them onto the drum is limited to a pre-set maximum value.

Also, the tension threads will stretch under tension. By using the force limiter, one can take up the slack caused by this stretching, thereby ensuring complete folding.

Also, in certain embodiments according to the present invention, the force limiter is design as a component allowing patency because of its overall ring or tube shape. Hence, the force limiter can be designed to fit into very little space while allow the room it takes to used for other purposes as well. For example, a guide wire may be advanced through the inner lumen established by the elements forming the force limiter.

In some embodiments according to the present invention, one achievable advantage is that the implant must not be overly unfolded. In fact, because of the displacement limiter the tension threads cannot be released more than it was pre-set as the length by which the tension threads may be unwind is limited to a pre-set value by means of the displacement limiter. That way, the tension threads will not be over-released beyond the maximum diameter of the stent. Over-releasing causes the stent/valve to bounce up and down in the blood flow of the beating heart making positioning difficult. Over-releasing also poses a risk where the strings may come off the stent/valve. This may be advantageously avoided by the present invention.

In the following, the present invention will be exemplarily described with respect to the accompanying drawing. In the drawing, same reference numerals refer to same or identical elements. In the drawing.

Figure 1:
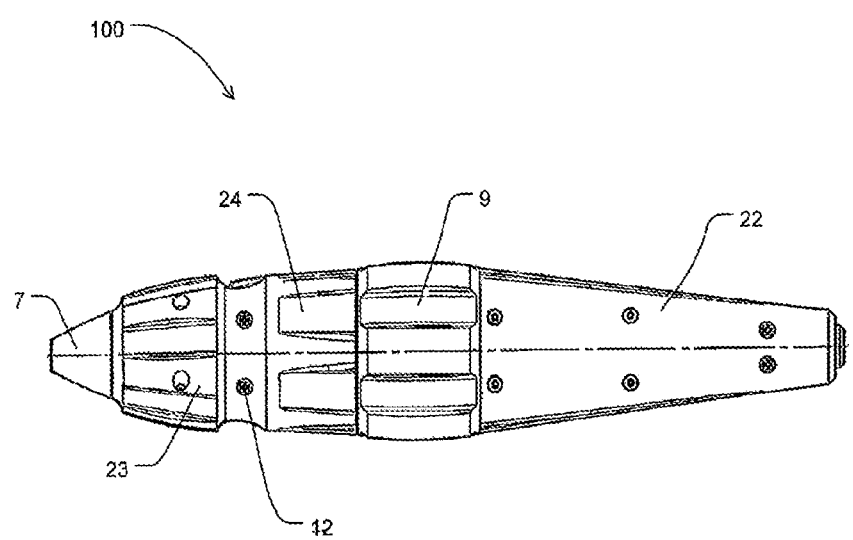
FIG. 1 shows a handle assembly according to the present invention in a side view.
Figure 2:
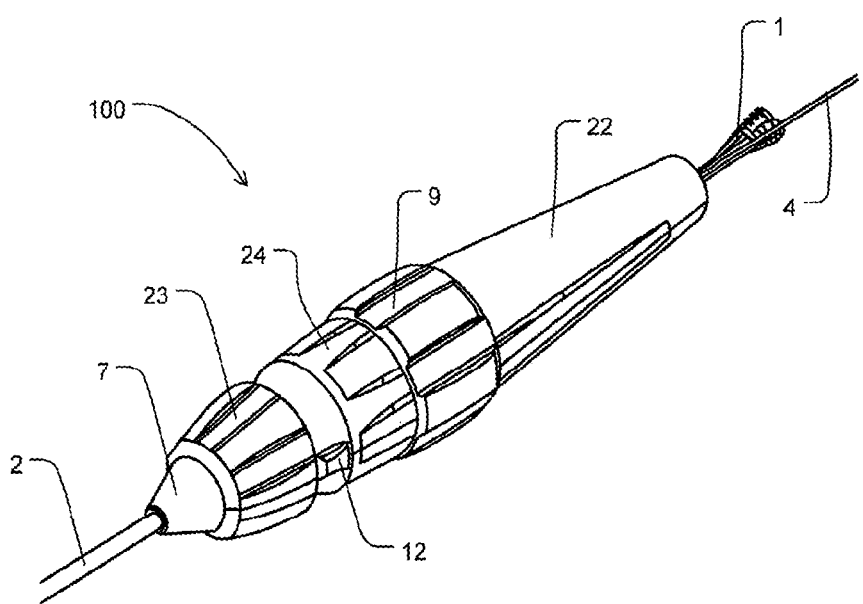
FIG. 2 shows the handle assembly of FIG. 1 in a perspective view.
Figure 3:
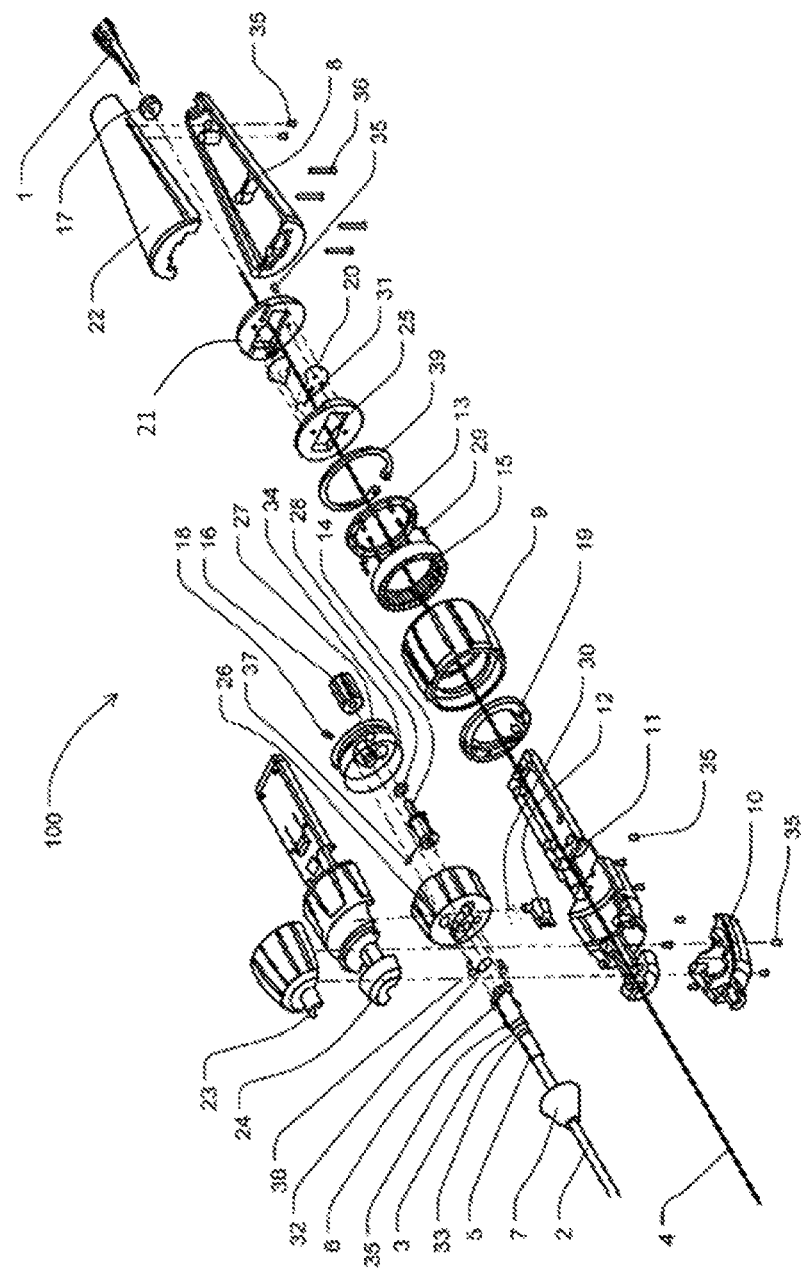
FIG. 3 shows the handle assembly of FIGS. 1 and 2 in an explosion view.
Figure 5:
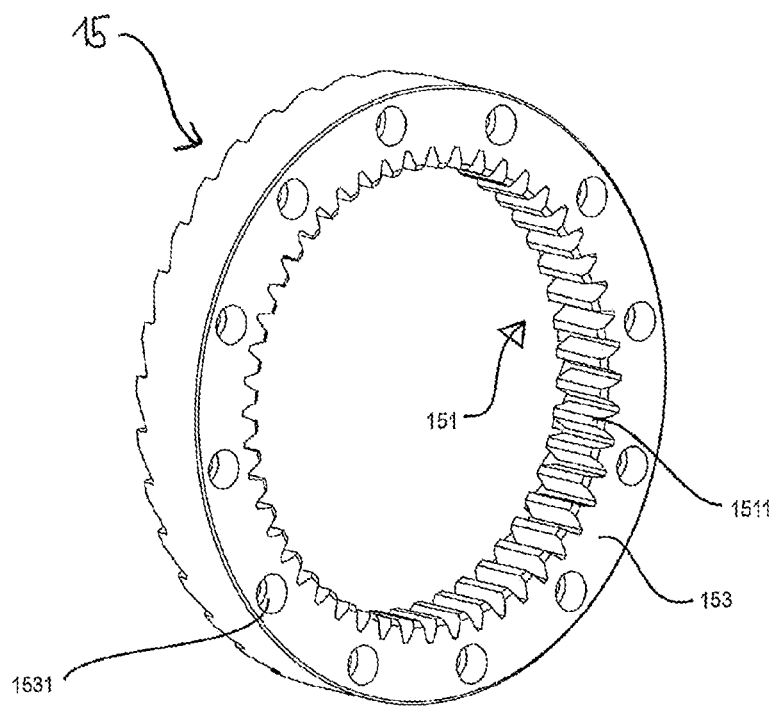
Figure 6:
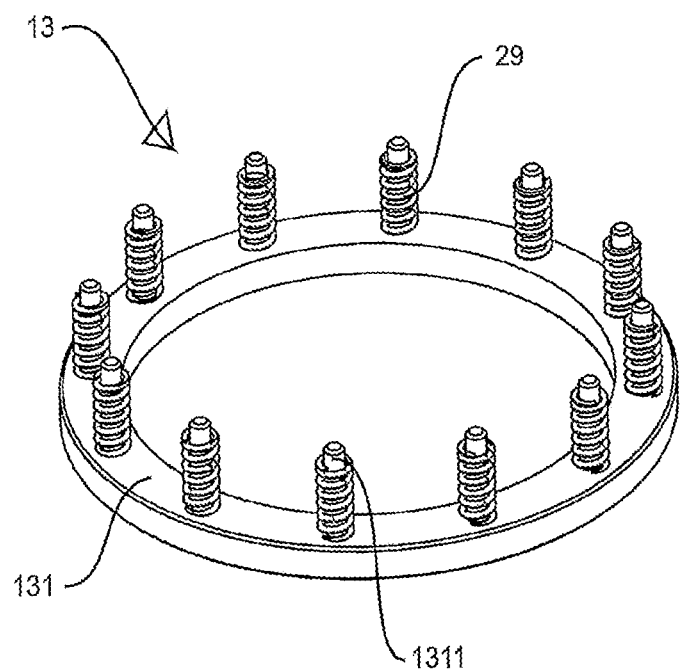
Figure 7:
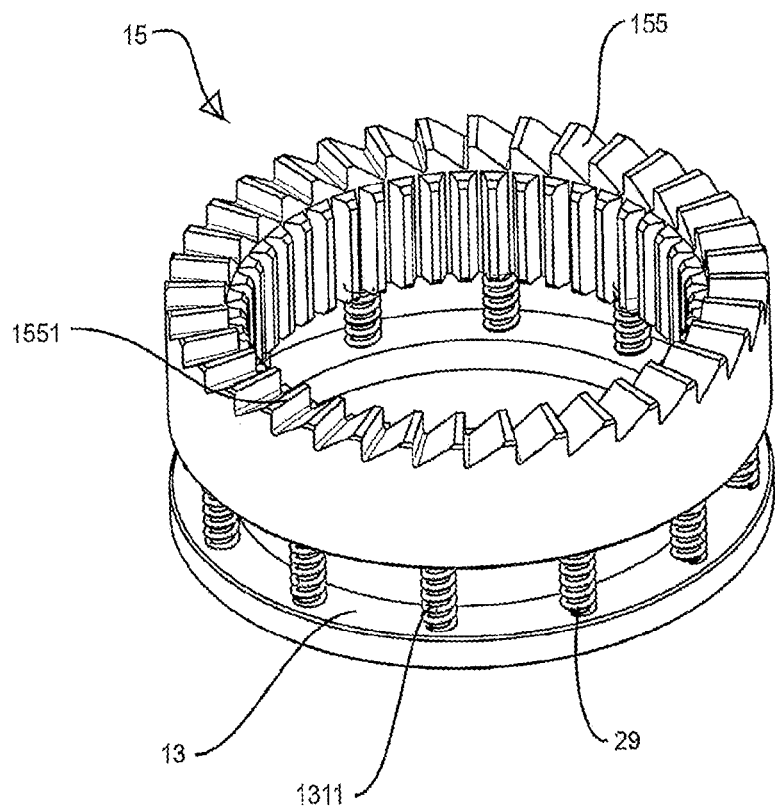
Figure 8:
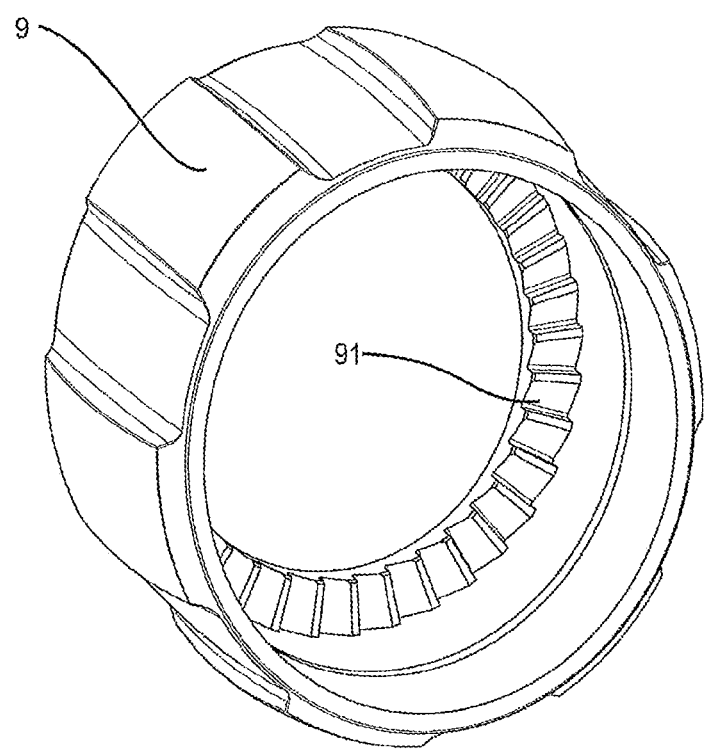
Figure 9:
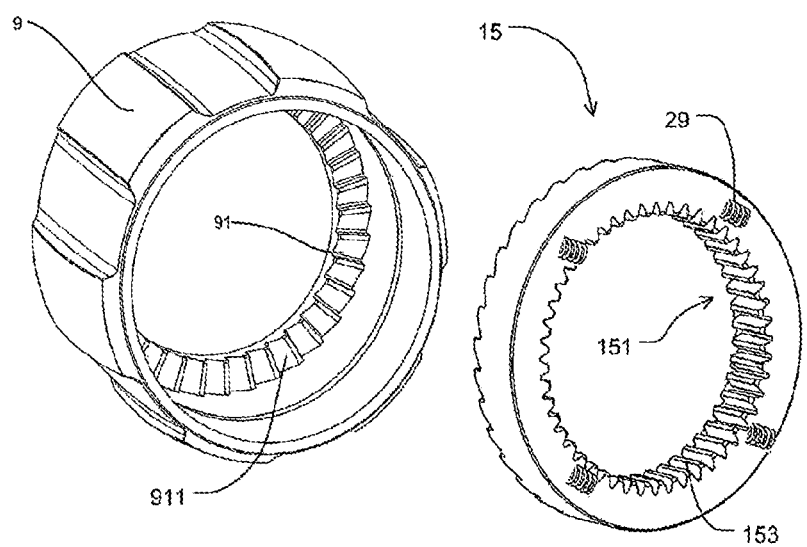
Figure 10:
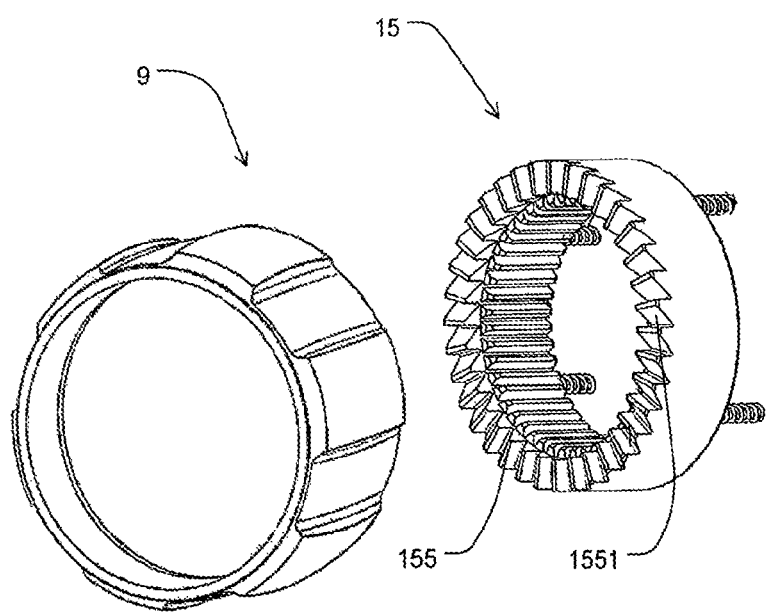
Figure 11:
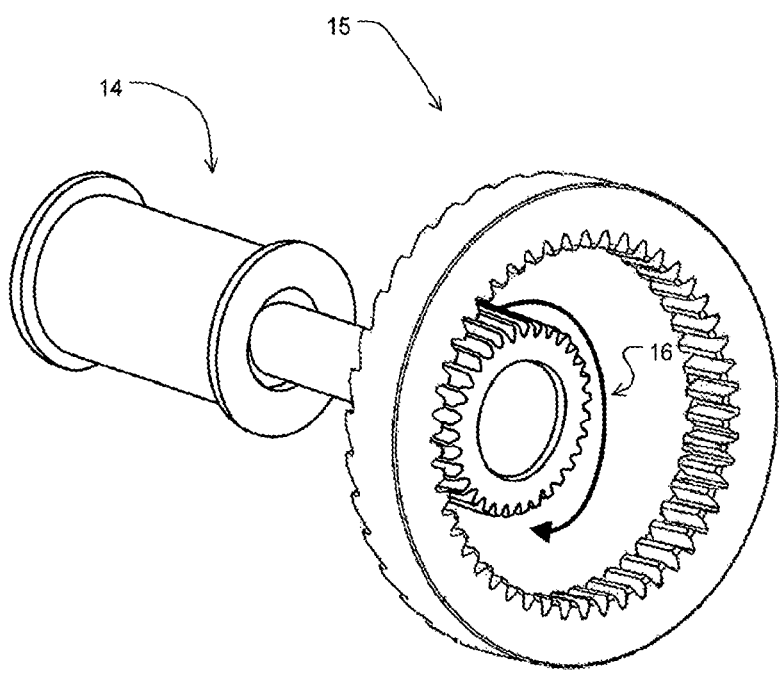
Figure 12:
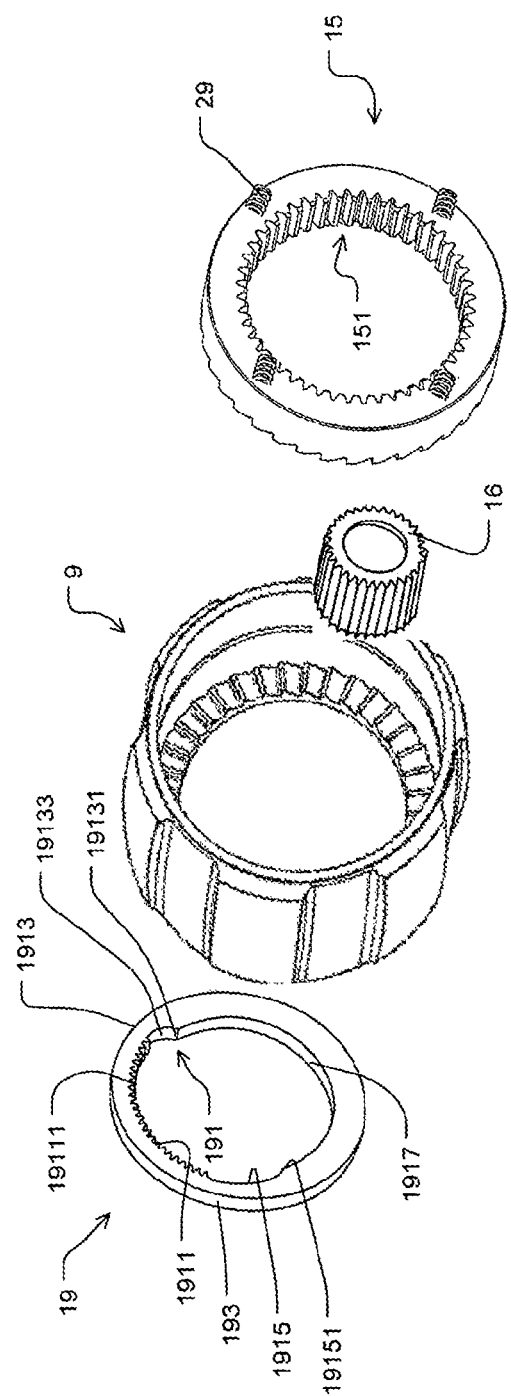
Figures 13A, 13B:
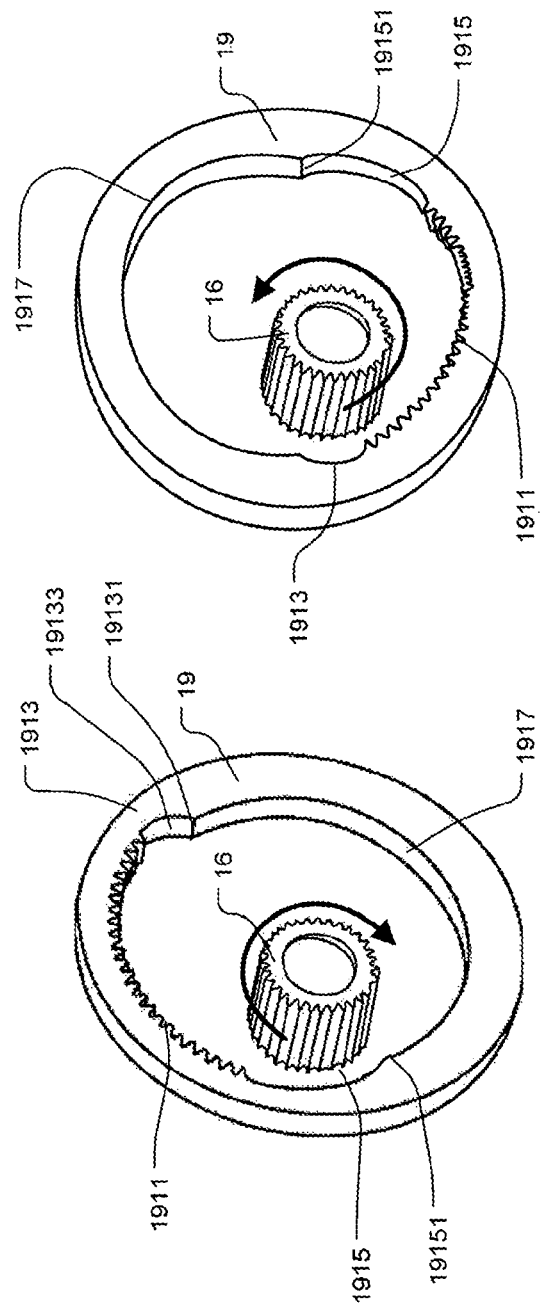
Figure 14:
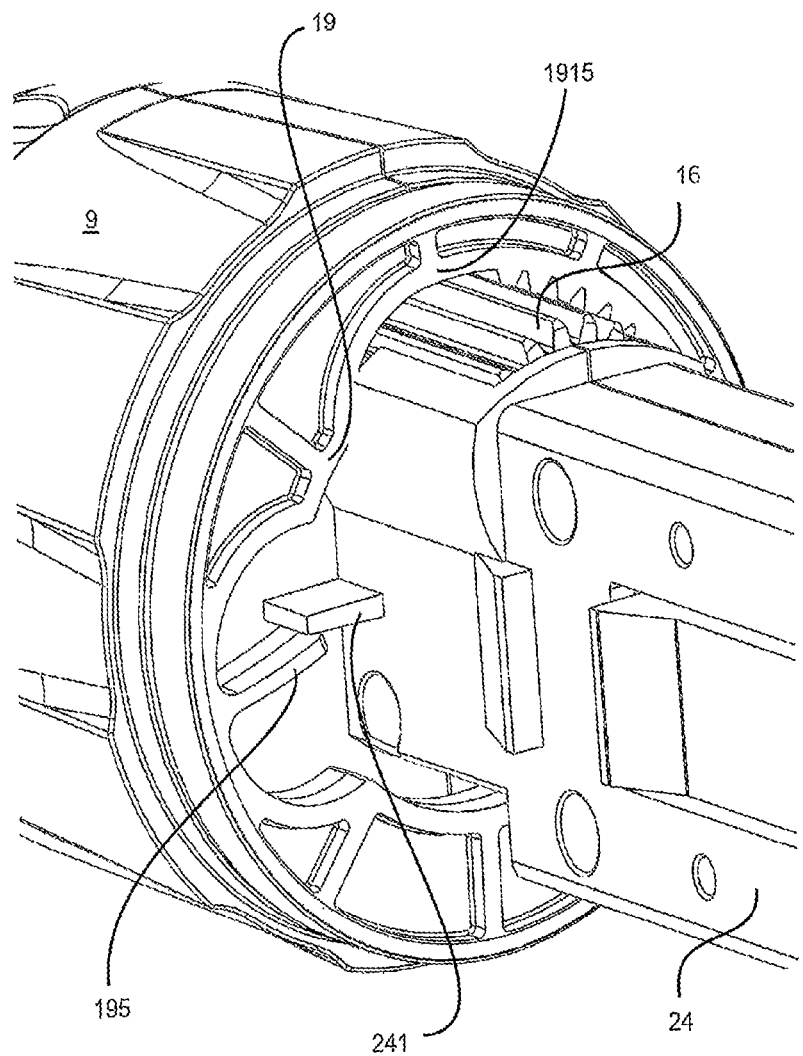
Figure 15:
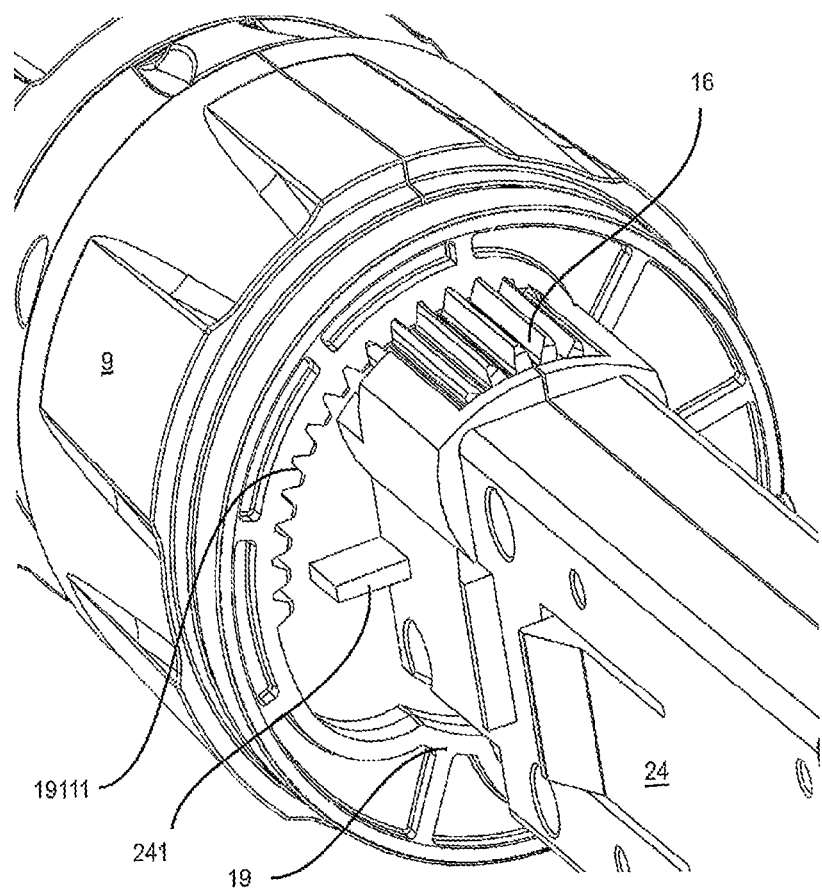
Figure 16:
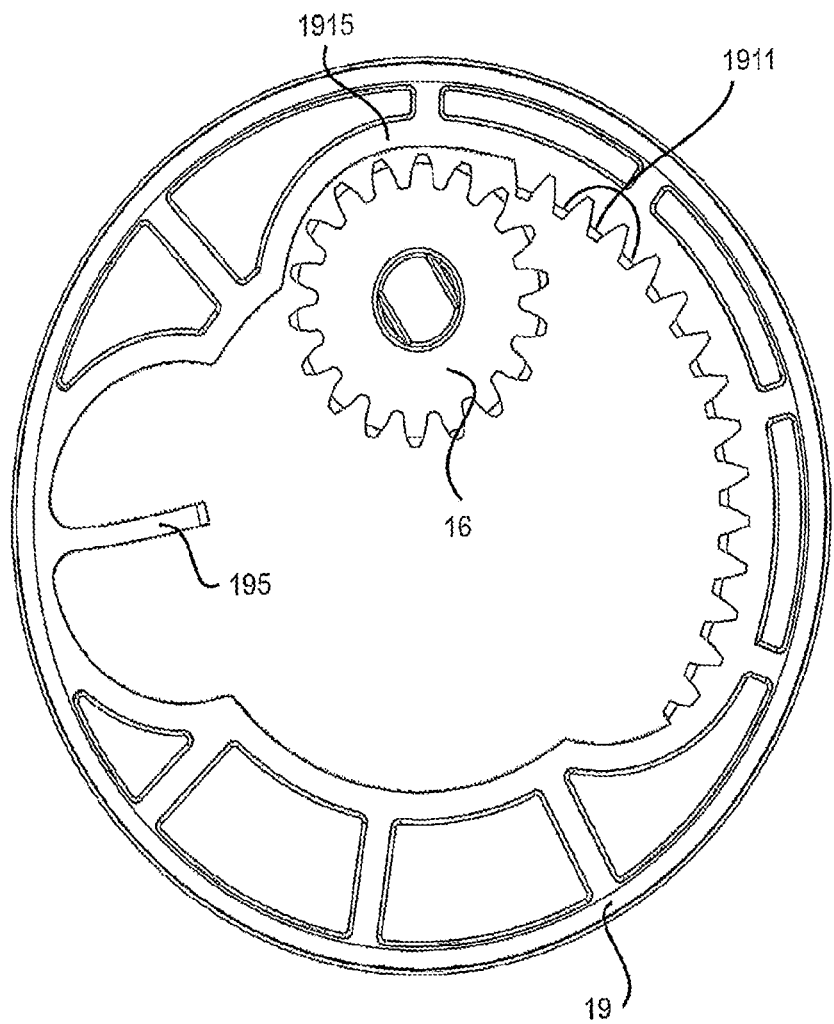
Figure 17:
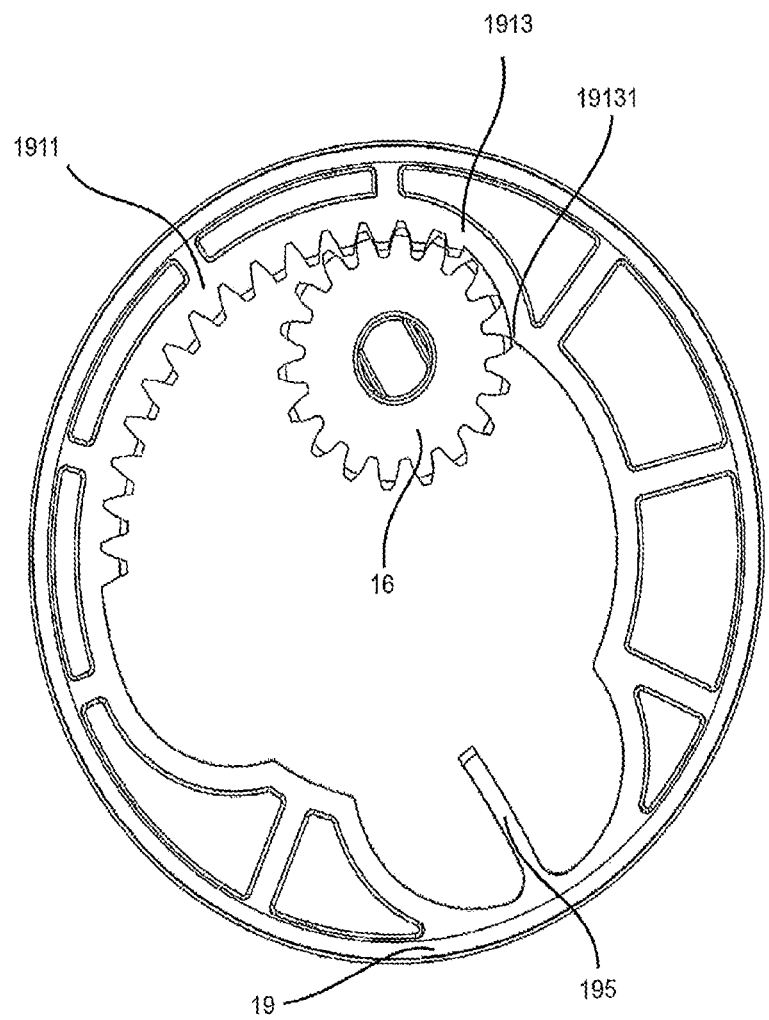
Figure 18:
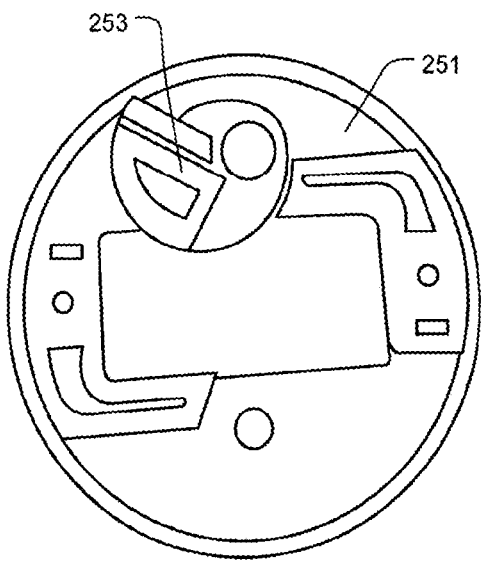
Figure 19:
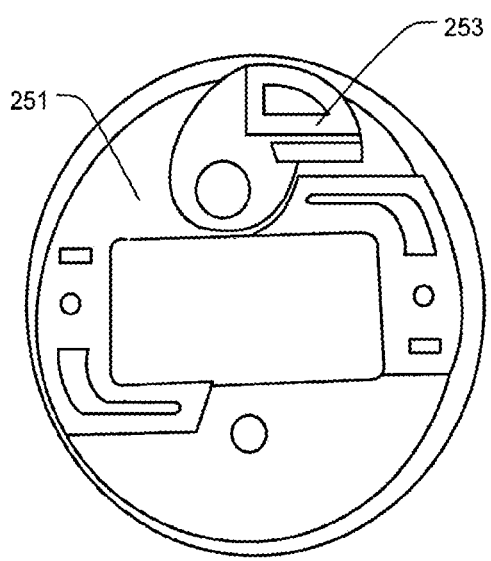
Figure 20:
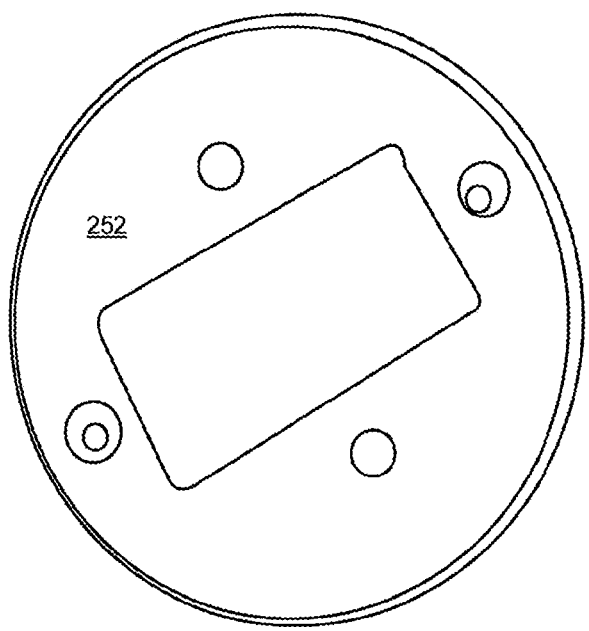
Figure 21:
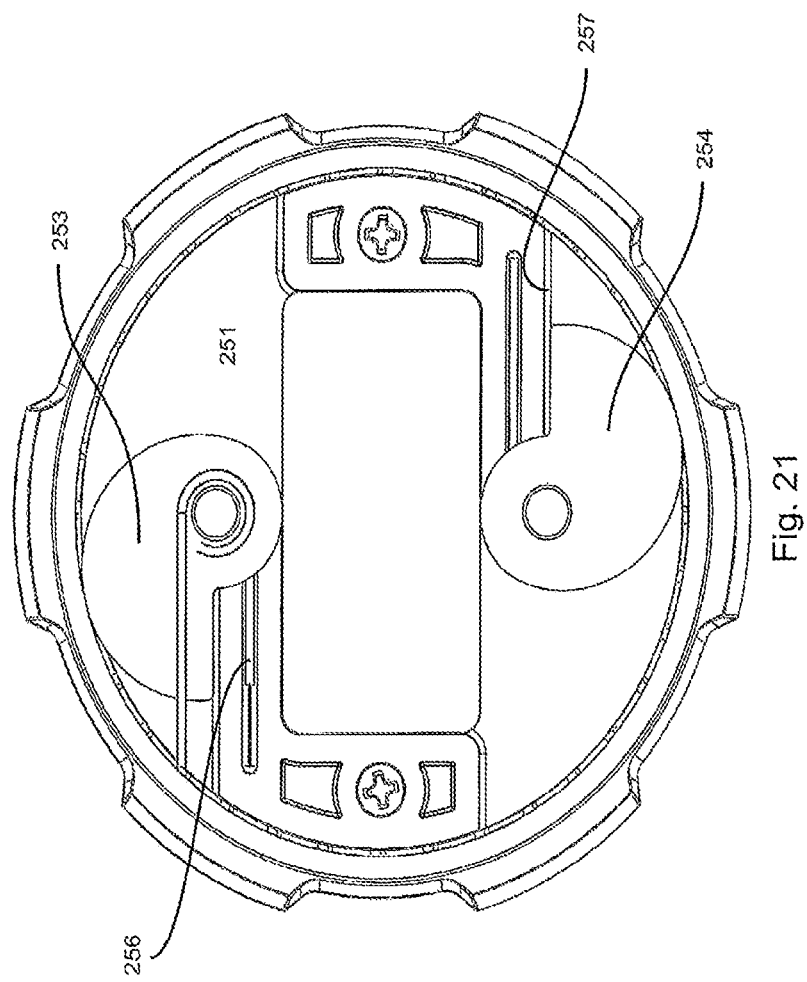

FIGS. 4a-d show different operating modes of the handle of FIGS. 1 to 3;

FIG. 5 shows a rush gear as part of the force limiter of the handle assembly of FIG. 1;

FIG. 6 shows a clutch stopper as part of the force limiter of the handle assembly of FIG. 1;

FIG. 7 shows the rush gear of FIG. 5 together with the clutch stopper of FIG. 6;

FIG. 8 shows the rear knob as part of the force limiter of the handle assembly of FIG. 1;

FIG. 9 shows the rear knob and the rush gear of the force limiter of the handle assembly of FIG. 1 in a first perspective view;

FIG. 10 shows the rear knob and the rush gear of FIG. 9 in a second perspective view;

FIG. 11 shows the rush gear of the force limiter of the handle assembly of FIG. 1 in connection with a drum for winding a tension thread in a perspective view;

FIG. 12 shows a stopper wheel or gear stopper as part of the displacement limiter of the handle assembly of FIG. 1 in a first embodiment;

FIG. 13a, b show the stopper wheel of FIG. 12 in engagement with a rush gear demonstrating the function of the stopper wheel;

FIG. 14 shows the stopper wheel or gear stopper of FIG. 1 in a second embodiment in a first state;

FIG. 15 shows the stopper wheel or gear stopper FIG. 14 in a second state;

FIG. 16 shows the stopper wheel of FIGS. 14 and 15 in a first plan view;

FIG. 17 shows the stopper wheel of FIGS. 14, 15 and 16 in a second plan view;

FIG. 18 shows parts of a brake frame assembly of the handle assembly of FIG. 1 in a first state;

FIG. 19 shows the parts of FIG. 18 in a second state;

FIG. 20 shows a cover to the parts of FIG. 18;

FIG. 21 shows the assembled brake frame assembly, however without a cover; and

Figure 22:
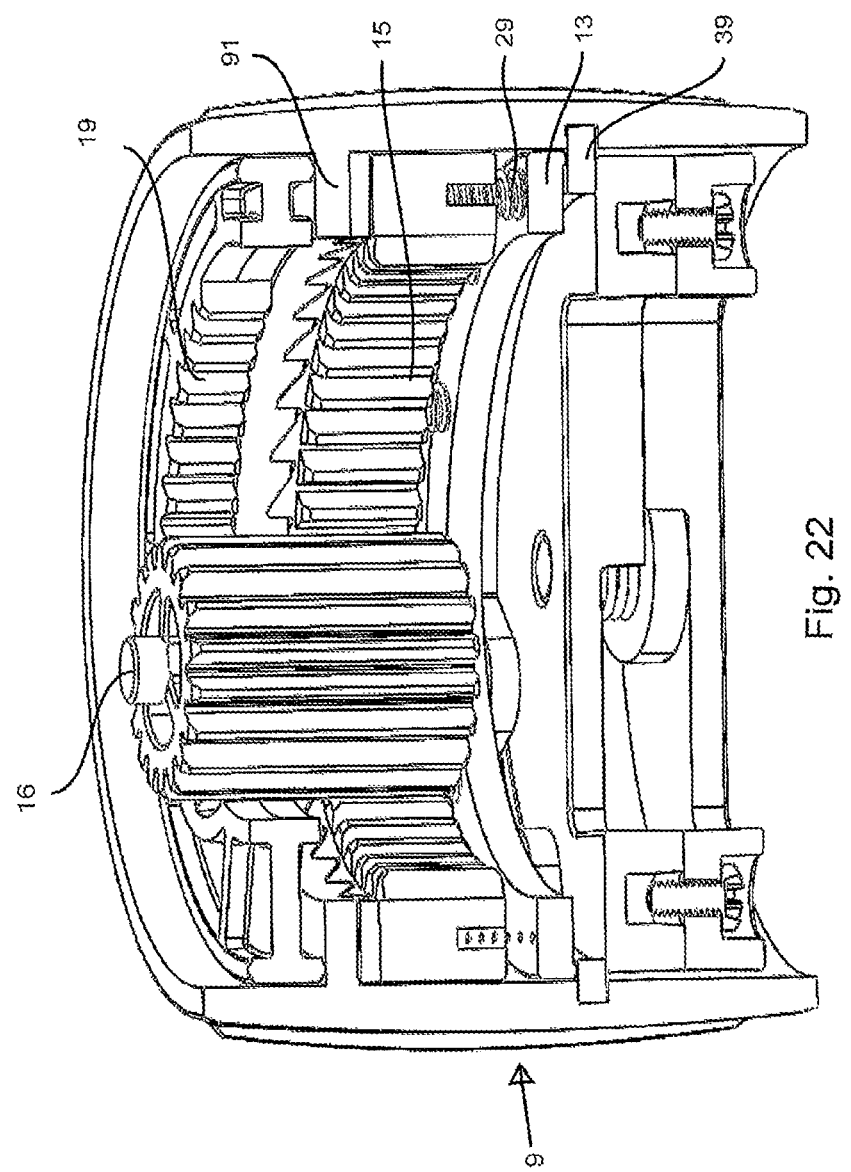

FIG. 22 shows a slightly perspective view of a longitudinal section of the rear knob of the handle assembly according to the present invention.

Figure 23:
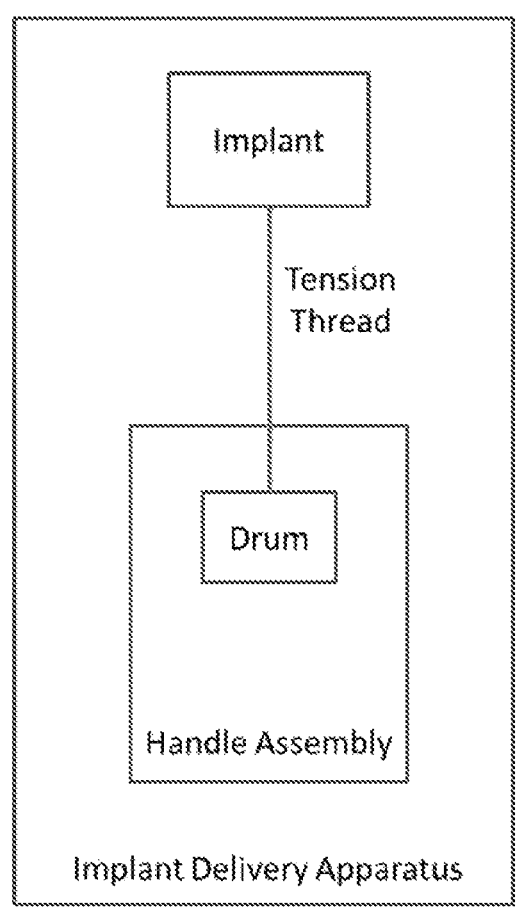

FIG. 23 is a schematic view of an implant delivery apparatus according to an embodiment of the present invention.

FIG. 1 shows a handle assembly 100 according to the present invention in a side view. In FIG. 1, a nose 7, a front knob assembly 23, a middle casing assembly 24 having a button 12, a rear knob 9, and a rear casing assembly 22 of the handle assembly 100 can be seen.

FIG. 2 shows the handle assembly 100 of FIG. 1 in a perspective view. In addition to what is shown in FIG. 1, in FIG. 2 the handle assembly 100 is connected a hub dummy 1, an outer tube 2 and an inner tube 4.

The inner tube 4 is in its front section arranged within the outer tube 2. The outer tube 2 may comprise further elements besides the inner tube 4 such as tension threads or strings (not shown) for folding and unfolding the implant (also not shown).

In certain embodiments according to the present invention, the outer tube 2 comprises a first connection device (not shown in the figures) configured to engage with a second connection device (also not shown in the figures) forming part of a detachable catheter tip carrying the implant. The first and the second connection device may be configured as plug-in connectors, as crests or crowns or the like, in all cases configured to engage with each other.

It goes without saying that with respect to the present invention, the handle assembly does not need all elements shown in FIG. 1 or 2. For example, the present invention can also be carried out with a handle assembly (not shown) which comprises just the rear knob 9, and a rear casing assembly 22. All other elements described herein are optional. For that reason, whenever it is referred to the hub called "rear" knob 9 herein, it is to be understood that the term "rear" has been added in order to distinguish the (rear) knob 9 from the (front) knob 23. Hence, the rear knob 9 could also be simply referred to as "knob" (without "rear"). The same applies to the rear casing assembly 22 which could as well be addressed as "casing assembly 22".

FIG. 3 shows the handle assembly 100 of FIGS. 1 and 2 in an explosion view. As stated with regard to FIGS. 1 and 2, the handle assembly 100 may comprise all or only some of the elements shown in FIG. 3. It may even consist of those elements. However, the handle assembly 100 may as well comprise further elements in addition to the ones disclosed in FIG. 3.

Further, according to the embodiment according to the invention shown in FIG. 3, some or all of the elements shown in FIG. 3 may be arranged in the handle assembly 100 in the order or relation to each other shown in FIG. 3. However, the order may be amended in any arbitrary manner as long as the function of the handle assembly 100 or certain sections thereof is still ensured according to the understanding of the skilled person.

As can be seen from FIG. 3, the front knob assembly 23, the middle casing assembly 24, the rear knob 9, and the rear casing assembly 22 each are comprised or accompanied by further elements.

In particular, the front knob assembly 23 comprises a front knob 10 covering a first rod fitting 5 and a second rod fitting 6, the first one being larger than the second one. It comprises another tube 3, a first o-ring 32 (may be metric), a second o-ring 33 (may be metric), several pan heads 35, also known as pan-head screws, (may be M2×0.4), and a sealing pan head 38 (may be M3×0.5).

The front knob 10 may also cover sections of the middle casing assembly 24. The middle casing assembly 24 comprises a middle casing 11, a button 12, a torsion spring 30, sealed chamber assembly 26, a hex socket set screw 37 (may be M3×0.5), a drum 14 for winding thereon the tension threads used for folding/unfolding of the implant (not shown), a shaft seal 28, a seal chamber pin 18, an o-ring 34 (may be metric), a sealed chamber cover assembly 27, and a rush gear 16.

Parts of the casing assembly 24 are also covered by the rear knob 9. The rear knob 9 comprises a gear stopper 19, a rush gear 15 as an example of the first ring element mentioned above and below, some compression springs 29 as one example of a spring element, a clutch stopper 13 (or drive wheel) as an example of the second ring element mentioned above, and an internal retaining ring 39. It also comprises a groove for receiving the retaining ring 39 in its inner surface.

The rear casing assembly 22 comprises a rear casing 8 covering an end 17, a brake frame assembly 25, a torsion spring 31, two brake pads 20, a brake frame 21, some pan heads 35 (may be M2×0.4), and some pan heads 36 (may be M2×0.4).

As is evident to the skilled person, the feature combination described with respect to FIG. 3 is not the only possible one. In fact, some elements shown in FIG. 3 may be waived upon manufacturing a handle assembly according to the present invention as long as the invention as defined in its most general way, see above, or by the appended claims is still reflected by the so composed handle assembly. For that reason, the number of the single elements and their arrangement relative to each other shown in FIG. 3 is to be understood as just one possible embodiment according to the present invention. Thus, the handle assembly according to the present invention may comprise any arbitrary combination of features shown in FIG. 3 or even not shown.

Also, whenever some elements have been attributed to a particular component discussed with reference to FIG. 1 it has to be understood that certain elements may as well have been attributed to another component shown in FIG. 1. Also, some elements certainly may be attributed to at least two adjacent components at the same time as they extend through at least two neighboring components.

FIGS. 4a-d show different modes for operating of the handle of FIGS. 1 to 3 according to certain embodiments of the invention.

Figure 4A:
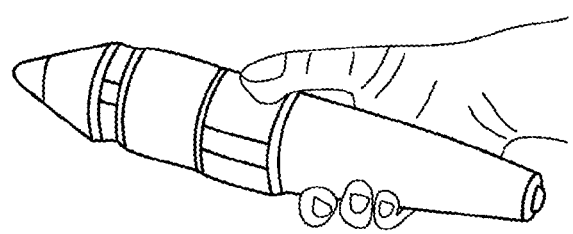

FIG. 4a shows how the handle assembly 100 can be held while simultaneously rotating the rear knob 9 by the operator's thumb. That way, the implant can advantageously be folded or unfolded by using just one hand.

Figure 4B:
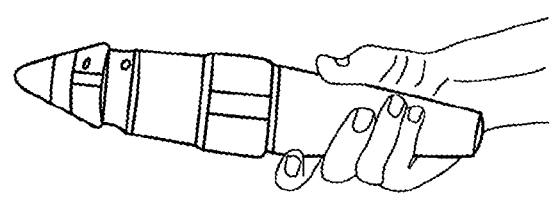

FIG. 4b shows how the handle assembly 100 may be held without effecting the operation sections thereof. By rotating the rear casing assembly 22 about its longitudinal axis as is indicated in FIG. 4b, the implant (not shown but connected to the outer tube 2) is also being rotated. Hence, the implant may be properly arranged at the site of its implantation, for example within the heart, by rotating the handle assembly 100.

Figure 4C:
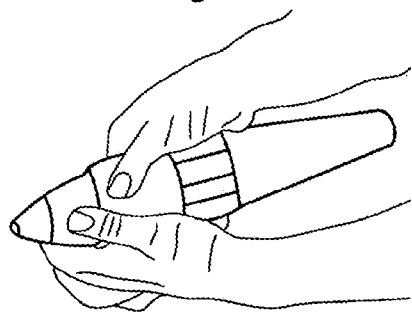

FIG. 4c shows how the button 12 is being pressed (by the thumb of the right hand). Pressing the button 12 allows the front knob assembly 23 to be rotated (by, for example, the left hand as shown in FIG. 4c) about its longitudinal axis while the button 12 is being pressed or once the button 12 was pressed. As long as the button 12 is not depressed or was not pressed, the front knob assembly 23 may not be rotated. The outer tube 2 comprising the first connection device is interconnected with the front knob assembly 23 such that rotating the latter results in simultaneously rotating the outer tube 2 and the first connection device as these elements are fixed to each other in a compulsory guiding such that one cannot rotate while one of the other elements does not rotate. In particular embodiments, rotating the outer tube 2 results in de-clamping of at least one tension thread (not shown) and in releasing it from the implant and/or from the implant delivery device. Hence, the button 12 prevents accidental rotation of the outer tube 2 and, hence, in said particular embodiments, unintended de-clamping of the tension thread. In other embodiments according to the present invention, rotating the outer tube 2 may have a different effect. For example, rotating may activate a cutter used for cutting the tension thread.

It is obvious to the skilled person that any other activation or deactivation device that allows or forbids rotation of the front knob assembly may be provided instead of the button 12 which only serves as an example.

Figure 4D:
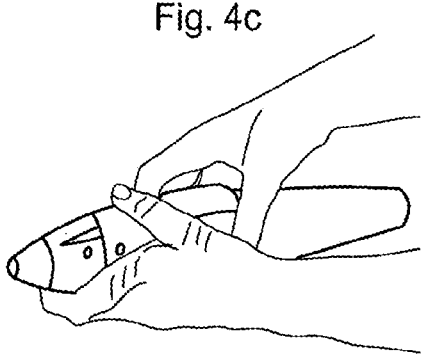

FIG. 4d shows an alternative way of holding the handle assembly 100 with two hands.

FIG. 5 shows a perspective view onto the lower surface of a rush gear 15 forming part of the force limiter of the handle assembly 100 of FIG. 1. The rush gear 15 is a ring-shaped element comprising teeth 1511 arranged at its inner surface 151.

The lower or bottom surface 153 of the rush gear 15 comprises the openings of at least two receptions 1531 which extend in a direction perpendicular to the lower surface 153.

FIG. 6 shows a perspective view onto the clutch stopper 13 as part of the force limiter of the handle assembly 100 of FIG. 1.

On its upper surface 131 the clutch stopper 13 comprise a number of pins 1311 (or extrusions or protrusions) extending (preferably perpendicularly) from the upper surface 131. The pins 1311 (whose number may assume, for example, any value between two and 20, preferably 11 or 12) are provided to protrude into the receptions 1531 of the lower surface 153 of the rush gear 15 shown in FIG. 5.

Compression springs 29 (or any other elastic element or material) are provided in the upper surface 131 of the clutch stopper 13. In particular embodiments according to the present invention, the compression springs 29 are arranged over all or some of the pins 1311.

The embodiment of FIG. 6 comprises twelve compression springs 29. However, their number may vary according to need.

Internal tests have shown that twelve compression springs 29 like the ones shown in FIG. 6 are able to provide an appropriate clutch opening force of 25 N.

In practice, the number and size of the compression springs 29 will depend on the surface finish and the clearance between the matching parts.

FIG. 7 shows the rush gear 15 of FIG. 5 together with the clutch stopper 13 of FIG. 6. As can be seen from FIG. 7, the pins 1311 of the clutch stopper 13 fit into the receptions 1531 of the rush gear 15.

As can also be seen from FIG. 7, an upper surface 155 of the rush gear 15 comprises teeth 1551 or saw-like or wedge-shaped elements acting as clutch elements.

FIG. 8 shows the rear knob 9 (also referred to as hub) as part of the force limiter of the handle assembly 100 of FIG. 1, again in a perspective view revealing the inner space or the inside of the rear knob 9.

As can be seen from FIG. 8, the rear knob 9 comprises an inner rim 91 protruding into the inner space or the lumen of the patency of the rear knob 9. On its lower surface the inner rim 91 comprises teeth or saw-like or wedge-shaped elements acting as clutch elements.

In use, i.e., in the assembled stated, the rush gear 15 will be inserted into the lumen of the rear knob 9 such that the teeth 1551 of the rush gear 15 will contact the teeth 911 (see FIG. 10) of the inner rim 91 of the rear knob 9 as is shown in FIGS. 9 and 10. That way, the teeth 911 of the rear knob 9 and the teeth 1551 of the rush gear 15 will form together a clutch. The force needed to release the teeth 911 of the rear knob 9 from the teeth 1511 of the rush gear 15 or to disengage them from each other such that no rotation will be transmitted any more by contact of the teeth of the contacting elements depend on the strength of the compression springs 29 discussed with respect to FIG. 7. In any case, the teeth concerned are formed such that the clutch opens beyond a certain resistance against rotation.

FIG. 9 shows the rear knob 9 and the rush gear 15 (also referred to as a drive wheel) of the force limiter of the handle assembly of FIG. 1 in a first perspective view. In the embodiment of FIG. 9, the compression springs 29 are attached to the rush gear 15.

FIG. 10 shows the rear knob 9 and the rush gear of FIG. 9 in a second perspective view. As in FIG. 9, in FIG. 10 the two elements are shown in a sort of an explosion drawing showing how they are to be arranged to each other upon assembling the handle assembly 100.

The rush gear 15 and the rear knob 9 are linked together with the flat gear pattern or teeth 911 comprised by the inner rim 91 at the lower surface thereof, and the teeth 1551. In use, the rush gear 15 is pushed against the inner rim 91 by the compression springs 29 (or any other type of springs or elastic element) strong enough to maintain the connection until a pre-set threshold force is exceeded (for example, 25 N or 40 N). Above that, the compression springs 9 are not strong enough and the rush gear 15 disengages from the inner rim 91 to avoid breaking the tension thread (or string or cable or wire). This way, the force limiter limits the force or tension applied or applicable onto the tension thread(s).

The force limiter may include the internal retaining ring 39 shown in, e. g., FIG. 3 and FIG. 22.

FIG. 11 shows the rush gear 15 in engagement with another rush gear 16 (also referred to as a pinion). The pinion comprises teeth on its outer surface which engage with teeth 1511 on the inside surface 151 of the rush gear 15 and is rotated when the rush gear 15 rotates. The drum 14 is in turn connected to the rush gear 16 such that it is rotated once the rush gear 16 rotates.

At least one of the drum 14 and the rush gear 16 are arranged so as to rotated within the rear knob 9 or within the gear stopper 19 in an excentric manner (see also FIGS. 14-17).

The drum 14 is arranged to wind the at least one tension thread (not shown in the figures).

FIG. 12 shows the stopper wheel or gear stopper 19 in a first embodiment thereof as part of the displacement limiter of the handle assembly 100 of FIG. 1.

The gear stopper 19 is adapted to fit into the lumen of the hub or rear knob 9. It may be arranged within the rear knob 9 such as to rest on the upper surface of the inner rim 91.

The gear stopper 19 may have a ring or a tube shape enclosing an inner lumen or section by an inner surface 191. The inner surface 191 has at least two different sections or surface qualities or surface features. In other words, the inner surface 191 is not homogeneous.

The gear stopper 19 comprises a rib extending from its inner surface towards the inner lumen or section of the gear stopper 19. However, also present, the rib is not shown in FIG. 12 or 13. It is, however, shown in FIG. 3, and also in FIGS. 14-17.

In the example of FIG. 12, at a first section 1911, the inner surface 191 comprises teeth 19111. In a second section 1913, the surface 191 comprises no teeth. In the example shown in FIG. 12, the second section 1913 merely optionally has a width (extending from the inside surface 191 to an outside surface 193 of the gear stopper) that is the same (or almost the same) as the width of the first section 1911 (measured from the outside surface 193 to the bottom or origin of the teeth 19111. The teeth 19111 correspond to the teeth of the rush gear 16 such that the rush gear 16 may be moved along the first section 1911 or rotated by the first section 1911. That way, the rush gear 16 also shown in FIG. 12 may as well be moved over from the first section 1911 where its teeth are in contact with the teeth 19111 to the second section 1913 where only some teeth of the rush gear 16 are in contact with the teeth 19111 of the first section 1911, while some teeth of the rush gear 16 are not in contact any more. Since some teeth of the rush gear 16 are still in contact with the teeth 19111 of the gear stopper 19 when the rush gear 16 has reached the second section 1913, the rush gears 16 can be brought back from the second section to the first section by means of the matching teeth by simply changing its rotational direction.

The second section 1913 is adjacent to the first section 1911 or contacts it (as a neighboring section).

As can be seen from FIG. 12, the second section 1913 is more or less a recess 19133 or inclined surface which is delimited or bordered by the last tooth of the first section 19111 on one side and by an inclination or edge 19131 delimiting the opposite side of the recess 19133 defining the second section 1913.

Instead of the edge 19131 or protrusion or the like, any device might be used for stopping a further movement of the rush gear 16. For example, the second section 1913 might as well (or alternatively) have a stop, an inclination, a broader (in a radial direction) subsection, or the like, as long as the stop, an inclination, a broader (in a radial direction) subsection, or the like engages with the teeth of the rush gear 16 such that it prevents further rotation (even without lateral movement) of the rush gear 16. That way, the edge, the stop, the inclination, the broader (in a radial direction) subsection, or the like does engage with at least one of the rush gears' teeth.

The second section 1913 has a length (in a circumferential direction) such that the diameter of the rush gear 16 is large enough to engage with at least one (preferably more that one) teeth 19111 of the first section 1911 and, at the same time, to contact or to reach the edge 19133 delimiting the recess 19133. That way, once the rush gear 16 is positioned within the second section 1913, a further movement of the rush gear 16 away from the first section 1911 (i.e., in the clockwise direction in FIG. 12) is prevented, either by the edge or by the inclination shown in FIG. 12. At the same time, since it is still in contact with at least one tooth of the first section 1911 as explained above, it can always be rotated by the teeth 19111.

In the particular and exemplary embodiment of FIG. 12, the inner surface 191 additionally comprises a third section 1915 and a fourth section 1917.

The third section 1915 may be designed like the second section 1913 in that it has the same width (or radius) and/or an inclination and/or also no teeth. However, the second section 1913 and the third section 1915 may differ in their length and/or other geometrical features. Also, like the second section 1913 the third section 1915 may also contact the first section 1911, for example as shown in FIG. 12 (the second and the third sections are arranged at opposite ends of the first section).

The third section 1915 may be longer than the second section 1913.

Also, like the second section 1913, the third section 1915 may have an inclination, edge 19151, protrusion or the like, or any device might be used for stopping a further movement of the rush gear 16. For example, the second section 1913 might as well (or alternatively) have a stop, an inclination, a broader (in a radial direction) subsection, or the like.

Like the second section 1913, the third section 1915 limits the movement of the rush gear 16 by means of an edge or the like contacting the rush gear' teeth. As can be seen in FIG. 12, the further movement (in a lateral or circumferential direction along the inner rim of the stopper gear 19) of the rush gear 16 is restricted or stopped by a stop, an inclination, a broader (in a radial direction) subsection, or the like, that does not contact the teeth of the rush gear 16. At the same time, the third section 1915 is not long enough to allow the teeth of the rush gear 16 to become disengage from all teeth 19111 of the first section 1911. Rather, the dimensions of the third section 1915 and the rush gear 16 are chosen such that at least or only the last tooth of the teeth 19111 of the first section 1911 will always remain half-engaged with the teeth of the rush gear 16. That way, the rush gear 16 can always be returned or moved back towards the first section 1911, again by simply changing the direction of rotation.

In contrast to the when the rush gear 16 is definitely one of blocked and inmobilized in the second section 1913, the rush gear 16, when positioned in the third section 1915, may still be rotated. When it is rotated away from the first section 1911, the last tooth will be repeatedly overleaped which results in a funny, machinery noise of teeth that do not properly engage with each other while being moved with respect to or along each other, also known from improper operation of car gear boxes upon changing gears.

The fourth section 1917 is also optional. It may be arranged opposite the first section 1911. It may or may not contact the first section 1911. It may have teeth or no teeth.

FIG. 13a shows the wheel stopper or gear stopper 19 in engagement with the rush gear or pinion 16. The rush gear 16 is positioned within the third section 1915, which is toothless. The gear stopper 19 is positioned within the rear knob or hub 9 without being fixed. Rather, the gear stopper 19 is held within the rear knob 9 acting as a casing for the gear stopper 19. The gear stopper 19 may, however, rotate within the rear knob 9 and relative thereto. Hence, when being further rotated in the direction indicated by the arrow by operating the rear knob 9, for lack of engaging teeth, the rush gear 16 cannot be rotated any further down. Also, the optionally provided inclination of the third section 1915 hinders the rush gear 16 to move further on along the inner surface of the gear stopper 19. This limits the rotatability of both the gear stopper 19 and the rear knob 9.

FIG. 13*a* shows how the gear stopper 19 and the rush gear or pinion 16 are positioned relative to each other in a state in which the implant is maximally folded.

In the state shown in FIG. 13*a*, the rib of the gear stopper 19 (only shown in FIGS. 14 and 15) abuts the rib of the rib of the casing, or the gear stopper 19 is stopped by the rib touching some element of the casing other than the rib, such that the gear stopper 19 can not be rotated any further. Hence, the rush gear 16 also can not be rotated any further. Thus, any intention of the user to rotate the knob any further must be in vain in that the rush gear 16 and, thus, the drum 14 will not be rotated any further and the tension thread will not be wound any further. Rather, what happens once the rush gear's rib has come to a halt is that the force limiter of the handle assembly 100 will come into play and the clutch comprised by the rear knob 9 will open against the force of the springs 29. In consequence, the rear knob 9 might still be rotated even if the rush gear 16 has entered the third section 1915. However, its rotation is no longer transmitted onto the drum 14 and the tension thread is no longer wound or further tensioned.

FIG. 13*b* shows how the gear stopper 19 and the rush gear or pinion 16 are positioned relative to each other in a state in which the implant is maximally unfolded. The rush gear 16 is positioned inside the second section 1913, which is toothless. Hence, when being further rotated in the direction indicated by the arrow by rotating the rear knob 9, for lack of teeth, the rush gear 16 cannot be rotated any further.

In the state shown in FIG. 13*b*, if the user should intend to further rotate the rear knob 9 once the rush gear 16 has entered the second section 1913, the rush gear 16 would not get over the inclination or edge 19133. Rather, the inclination or edge 19133 would block any further rotation of the rush gear 16 and the drum 14, wherefore the tension thread can not be released any further. That way, the displacement of the tension thread is limited. The rush gear 16 would not slip or turn freely as it does inside the third section 1915 as described supra. The ribs discussed above are not in contact with each other in this state. Also, the force limiter or its clutch does not open. No noise of slipping teeth will be heard.

FIG. 14 shows a stopper wheel as part of the displacement limiter of the handle assembly of FIG. 1 in a second embodiment and in a first state.

In contrast to the FIGS. 12, 13*a* and 13*b*, the protrusion of the gear stopper 19 which may be a rib, is shown in FIG. 14. It is depicted with reference numeral 195. The rib, also referred to as spring rib, protrudes into the lumen of the gear stopper 19.

As can be seen in FIG. 14, in this embodiment only, the rear part of the middle casing assembly 24 also comprises a protrusion, e. g. a rib, referred to as hereinafter as second rib 241. The second rib 241 is arranged on the casing, and the first rib 195 is arranged on the gear stopper 19 such that the first rib 195 is placed at the left side (or above the second rib 241) when the gear 19 has reached the third section 1915 of the gear stopper 19.

It goes without mentioning that instead of the first and second protrusion any other form and shape a stop or a pair of matching stops will do as well, which is also encompassed by the present invention.

FIG. 14 shows the displacement limiter in a state in which the second rib 241 hinders the gear stopper 19 from being further rotated in the anticlockwise direction (related to the illustration of FIG. 14) because of the contact between the ribs 195 and 241. Hence, the tension thread cannot be wound any further by rotating in the anticlockwise direction. In FIG. 14, the rush gear 16 is positioned in the third section 1915. When positioned in the third section 1915 of this exemplary embodiment, the teeth of the rush gear 16 do not contact an inclination or stop or the like of the third section 1915. The movement of the gear stopper 19 is stopped only by the contacting ribs 195, 241. The rush gear 16 may rotate freely in one direction, but it cannot create relative movement between itself and the gear stopper 19.

FIG. 15 shows the stopper wheel or gear stopper 19 of FIG. 14 in a second state.

FIG. 15 shows the displacement limiter in a state in which the second rib 241 does not hinder the gear stopper 19 from being further rotated in the anticlockwise direction (related to the illustration of FIG. 14). Hence, the tension thread can not be unwound further by rotating in the clockwise direction. However, it cannot be released any more since the rush gear 16 is blocked in the second section 1913 as describe above. In FIG. 15, the rush gear 16 is positioned in the second section 1913.

FIG. 16 shows the stopper wheel of FIGS. 14 and 15 in a first plan view. In FIG. 16, the gear stopper 19 takes the position relative to the rush gear 16 it also takes in FIG. 14. As can be seen, the teeth of the rush gear 16 are not in full contact with the last tooth of the first section 1911. Rather, the last tooth is half-engaged so that upon rotating the rush gear 16 in the clockwise direction, its teeth will automatically get engaged again with the first tooth of the first section 1911 first and, in consequence, with the remaining teeth 19111 of the first section 1911 as well.

FIG. 17 shows the stopper wheel of FIGS. 14, 15 and 16 in a second plan view. In FIG. 17, the gear stopper 19 takes the position relative to the rush gear 16 it also takes in FIG. 15. As can be seen, the teeth of the rush gear 16 are still in full contact with not only the last tooth of the first section 1911. At the same time, the rush gear 16 contacts the edge 19131 of the second section 1913. Hence, the rush gear 16 that moves on a constant radium about a rotation axis extending through the center of the gear knob 19 may not be rotated further in the clockwise direction. It is blocked in the state shown in FIG. 17 regarding any further rotation in the clockwise direction. It may, however, be rotated in the anticlockwise direction.

FIG. 18 shows parts of a brake frame assembly 25 of the handle assembly of FIG. 1 in a first state which is a state before the brake frame assembly 25 has been fully assembled.

The parts brake frame assembly 25 which are shown in FIG. 18 are a first frame 251 and a first half-wheel 253, the latter being an example of a brake element. Other examples of the brake elements also encompassed by the present invention include a brake pad and a brake shoe.

The first half-wheel 253 is interconnected with the first frame 251 in manner such that the first half-wheel 253 may pivot relative to the first frame 251.

FIG. 18 shows not all parts of the brake frame assembly 25. In the exemplary embodiment shown only in parts in FIG. 18, the complete brake frame assembly 25 comprises not only the first frame 251 and the first half-wheel 253 but also a second frame (not shown in FIG. 18 but in FIG. 21 as second frame 252) and a second half-wheel (also not shown in FIG. 18 but in FIG. 21 as second half-wheel 254). Moreover, the assembly 25 comprises two springs 256, 257 which are also not shown in FIG. 18 but indicated in FIG. 3 and shown in FIG. 21. Finally, the first frame 251 and the second frame 252 are interconnected to each other by screws as shown in FIG. 3 and in FIG. 21.

In the assembled state, the first and second frames 251, 252 serve as covers that sandwich the two half-wheels 253, 254 and the two springs 256, 257 between them.

In the particular embodiment of FIG. 18, the first and second frames 251, 252 have a round periphery. Also, the brake frame assembly 25 has an through-opening in its center, which may be rectangular in shape. The rectangular shape shown in FIG. 18 is configured to correspond to the cross section of the middle casing assembly 24.

As stated above, none of the two springs 256, 257 (or other elastic elements) of the brake frame assembly 25 are shown. In practice, one of these springs is attached between the first half-wheel 253 and the first frame 251 such that the spring keeps the half-wheel 253 in the position relative to the first frame 251 as shown in FIG. 18. The other spring will do the same with the second half-wheel (not shown in FIG. 18) in the lower part of FIG. 18.

In the exemplary embodiment of FIG. 18, the springs are inserted into grooves seen in FIG. 18. However, any suitable protrusion or the like will do as well.

In the example of FIG. 18, the springs are selected and arranged so as to stay open as it is shown in FIG. 18 such that it takes effort to close its spring arms (whereas with other springs it needs effort to open them). That means it takes effort to bring the first half-wheel 253 shown in FIG. 18 into its position shown in FIG. 19. The position of the first half-wheel 253 shown in FIG. 18 does not reflect its position in a fully assembled state of the brake frame assembly 25.

It goes without explanation that instead of two springs and two brake elements one of each will also do.

FIG. 19 shows the parts of FIG. 18 in a second state. The second state shows the position of the half-wheel 253 in a fully assembled state of the brake frame assembly 25.

Although no springs are shown in FIG. 19, it can easily be understood that the curved surface of the half-wheel 253 may be urged over the outer shape or the circumference of the brake frame assembly 25, here exemplarily over the outer shape or the circumference of the first frame 251, and, in a full assembly state of the handle assembly 100, against an inner surface of the rear knob 9 inside of which the brake frame assembly 25 is arranged during use. Since the brake assembly 25 is arranged in a rotationally stable manner with respect to the middle casing assembly 24 such that the brake frame assembly 25 cannot rotate with respect to the handle assembly 100, whereas the rear knob 9 can, the first (and, if provided, also the second) half-wheel 253 causes friction and brakes the rotation of the rear knob 9. The degree of the braking effort certainly depends on the spring force and on the combination of the materials of the braking partners (i.e. the brake element and the inner surface of the rear knob 9). In any case, the braking efficiency will be chosen to be small enough so that the rear knob 9 still may be rotated by hand, and at the same time strong enough so that the memory shape effect of the implant or other forces applying to the implant or the tension thread(s) wound onto the drum 14 may not rotate the rear knob 9 by themselves.

FIG. 20 shows a cover to the parts of FIG. 18. It may be referred to as a second frame 252 in the sense discussed above with respect to the FIGS. 18 and 19.

FIG. 21 shows the almost fully assembled brake frame assembly 25 of the preceding figures. What is missing is the second frame 252. The assembly 25 is arranged within the rear knob 9. The springs 256, 257 press the half-wheels 253, 254 against the inner surface of the rear knob 9.

FIG. 22 shows a slightly perspective view of a longitudinal section of the rear knob 9 of the handle assembly 100 according to the present invention. The front part of the rear knob 9 is in the upper part of FIG. 22.

As can be seen in FIG. 22, the rush gear 16 is arranged within the rear knob 9 such that it engages with both the gear stopper 19 and the rush gear 15 of the force limiter.

FIG. 23 schematically shows an implant delivery apparatus according to an embodiment of the present invention.

REFERENCE NUMERALS 100 handle assembly
1 hub dummy
2 outer tube
3 tube
4 inner tube
5 first rod fitting
6 second rod fitting
7 nose
8 rear casing
9 rear knob
91 inner rim
911 gear pattern or teeth of inner rim
10 front knob
11 middle casing
12 button
13 clutch stopper
131 upper side
1311 pin or protrusion
14 drum
15 rush gear
151 inner surface
1551 teeth
153 lower surface
1531 reception
155 upper surface
1551 teeth
16 rush gear
17 end
18 seal chamber pin
19 gear stopper or stopper wheel or ring-shaped element
191 inner surface
1911 first section of the inner surface of the gear stopper
19111 teeth
1913 second section of the inner surface of the gear stopper
19131 edge
19133 recess
1915 third section of the inner surface of the gear stopper
19151 edge
1917 fourth section of the inner surface of the gear stopper
193 outer surface
195 first protrusion, e. g. a rib
20 brake pad
21 brake frame
22 rear casing assembly
23 front knob assembly
24 middle casing assembly
241 second protrusion, e.g. a rib
25 brake frame assembly
251 first frame
252 second frame
253 first half-wheel
254 second half-wheel
256 first spring
257 second spring 26 sealed chamber assembly
27 sealed chamber cover assembly
28 shaft seal
29 compression spring
30 torsion spring
31 torsion spring
32 metric o-ring
33 metric o-ring
34 metric o-ring
35 pan head
36 pan head
37 hex socket set screw
38 sealing pan head
39 internal retaining ring

The invention claimed is:

1. A handle assembly for an implant delivery device for folding or unfolding at least one medical implant through the use of at least one tension thread, wherein the handle assembly comprises:
 a drum for winding the at least one tension thread thereon by rotating the drum;
 a knob to be rotated by a user of the handle assembly in order to fold or unfold the medical implant by tightening or winding the at least one tension thread or by releasing or unwinding the at least one tension thread, the knob being arranged or interconnected with the drum such that the drum is rotated when the knob is rotated; and
 a displacement limiter for limiting the length or displacement by which the at least one tension thread may be at least one of wound onto or unwound from the drum by rotating the knob,
 wherein the displacement limiter comprises a gear stopper which is ring-shape or tube-shape, the knob and the gear stopper are coaxially assembled forming an assembled structure which has an axial through-hole at a center of the assembled structure thereof,
 wherein the gear stopper is arranged inside the knob wherein the gear stopper comprises a radially inner circumference and a radially outer circumference arranged opposite to each other, the radially inner circumference comprising at least a first section comprising teeth and at least one of a second section having an inner surface different than the inner surface of the first section or a radial width smaller than that of the first section and a third section having an inner surface different than the inner surface of the first section or a radial width smaller than that of the first section.

2. The handle assembly according to claim 1, wherein the drum and the knob are interconnected by a rush gear,
 wherein the rush gear is arranged to rotate inside the gear stopper along or by means of a gear pattern or teeth,
 wherein the rush gear is interconnected to the drum such a rotation of the rush gear results in a rotation of the drum.

3. The handle assembly according to claim 2, wherein at least one of the second section and the third section does not comprise teeth or a gear pattern.

4. The handle assembly according to claim 3, wherein at least one of the second section and the third section is arranged in contact with or adjacent to the first section.

5. The handle assembly according to claim 2, wherein at least one of the second section and the third section is arranged in contact with or adjacent to the first section.

6. The handle assembly according to claim 2, wherein the gear stopper comprises at least also a fourth section on its radially inner circumference, wherein the fourth section, is delimited from at least one of the first or second or third section by any one of an inclination, an edge, a stop or a protrusion which is configured to prevent the rush gear to be rotated further towards or onto the fourth section.

7. The handle assembly according to claim 6, wherein the gear stopper comprises at least a first protrusion arranged to interfere with a second protrusion of a casing assembly or any other element of the handle assembly so as to limit the rotation of the rush gear within the gear stopper.

8. The handle assembly according to claim 7, wherein the at least first protrusion is arranged so as to protrude from the radially inner circumference into the axial through-hole.

9. The handle assembly according to claim 8, wherein the at least first protrusion is arranged between the second and the third sections or at the fourth section or opposite the first section of the gear stopper.

10. The handle assembly according to claim 7, wherein the at least first protrusion is arranged between the second and the third sections or at the fourth section or opposite the first section of the gear stopper.

11. The handle assembly according to claim 7, wherein the third section has at least one of a length, width (in a radial direction) such that the rush gear may be positioned inside the third section such that one tooth of the rush gear is only half-engaged with at least one tooth of the teeth of the first section while at the same time the first protrusion and the second protrusion stop the gear stopper from rotating further.

12. The handle assembly according to claim 6, wherein the second section has at least one of a length, width (in a radial direction) and inclination such that the rush gear may be positioned inside the second section such that at least one tooth of the rush gear is engaged with at least one tooth of the teeth (19111) of the first section while at least one tooth of the rush gear is at the same time in contact with the inclination, the edge, the stop or the protrusion, wherein the inclination, the edge, the stop or the protrusion delimits the second section from the fourth section or is arranged within the second section.

13. The handle assembly according to claim 2, wherein the inner surface of at least one of the second section and the third section has a radial distance to a radial center of the gear stopper that is larger than a radial distance between tips of the teeth and the radial center of the gear stopper.

14. The handle assembly according to claim 2, wherein the drum is simultaneously engaged or half-engaged both to the rush gear and the gear stopper, or is in contact with one or both.

15. An implant delivery apparatus comprising at least one handle assembly according to claim 1, and further comprising a catheter.

16. The implant delivery apparatus according to claim 15, comprising at least one medical implant connected with the at least one tension thread for the purpose of folding and/or unfolding or provided or prepared for being connected with the at least one tension thread.

17. The implant delivery apparatus according to claim 16, wherein the at least one medical implant is a stent or a heart valve arrangement.

18. The handle assembly according to claim 1, wherein the drum and the knob are interconnected by a rush gear, the rush gear is arranged within the axial through-hole and is configured to rotate within the gear stopper in an eccentric manner.

19. The handle assembly according to claim 1, wherein the knob and the gear stopper are configured to rotate about a longitudinal axis of the axial through-hole independently from each other.

* * * * *